(12) United States Patent
Boss et al.

(10) Patent No.: US 7,632,637 B1
(45) Date of Patent: Dec. 15, 2009

(54) TECHNIQUE FOR ORIENTING AND BINDING PHAGE FOR BACTERIA DETECTION

(75) Inventors: Pamela A. Boss, San Diego, CA (US); Stephen H. Lieberman, San Diego, CA (US)

(73) Assignee: The United States of America as represented by the Secretary of the Navy, Washington, DC (US)

( * ) Notice: Subject to any disclaimer, the term of this patent is extended or adjusted under 35 U.S.C. 154(b) by 296 days.

(21) Appl. No.: 11/365,191

(22) Filed: Mar. 1, 2006

Related U.S. Application Data

(63) Continuation-in-part of application No. 10/895,470, filed on Jul. 19, 2004, now abandoned.

(51) Int. Cl.
*C12Q 1/70* (2006.01)
*C12N 7/00* (2006.01)

(52) U.S. Cl. .................................. 435/5; 435/235.1

(58) Field of Classification Search .................. None
See application file for complete search history.

(56) References Cited

U.S. PATENT DOCUMENTS 7,087,376 B2 * 8/2006 Miller ........................ 435/5
7,267,993 B2 * 9/2007 Pentrenko et al. ........... 436/518
2004/0191859 A1 * 9/2004 Tabacco et al. ............. 435/69.1

OTHER PUBLICATIONS

Mosier-Boss et al. "Use of fluorescently labeled phage in the detection and identification of bacterial species" Appl Spectrosc. Sep. 2003;57(9):1138-44.*

Sun, W. et al; "Food Borne Pathogens Use of bioluminescent *Salmonella* for assessing the efficiency of constructed phage-based biosorbent"; Journal of Industrial Microbiology & Biotechnology; USA, vol. 27, pp. 126-128 (2001).

Fleming, M. S. et al; "Stability and Exchange Studies of Alkanethiol Monolayers on Gold-Nanoparticles-Coated Silica Micropheres"; Langmuir; USA, vol. 17, pp. 4836-4843 (2001).

Borque, L. et al; "Latex Immunoassy of Beta2-Mocroblobulin in Serum and Urine"; Journal of Clinical Immunoassy; USA , vol. 17, pp. 160-165 (1994).

* cited by examiner

*Primary Examiner*—Christopher L Chin
*Assistant Examiner*—Christine Foster
(74) *Attorney, Agent, or Firm*—Ryan J. Friedl; Kyle Eppele

(57) ABSTRACT

A technique for orienting and binding the head end of phage to a substrate is disclosed. The tail end of the phage is thereby made readily available for bacteria sensing.

20 Claims, 5 Drawing Sheets
(3 of 5 Drawing Sheet(s) Filed in Color)

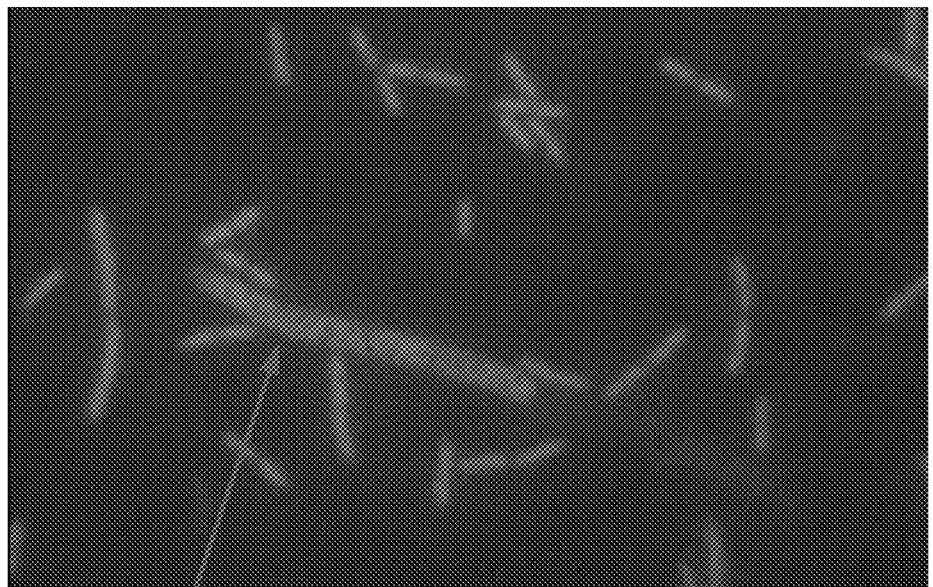
Bacillus  *FIG. 3a*
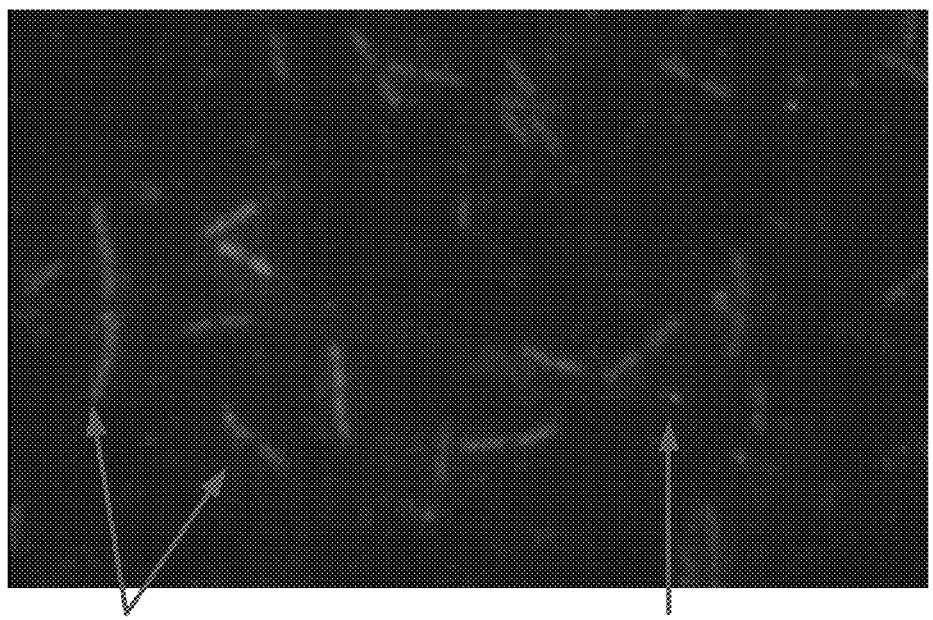
Salmonella  *FIG. 3b*  P22

TECHNIQUE FOR ORIENTING AND BINDING PHAGE FOR BACTERIA DETECTION

CROSS-REFERENCE TO RELATED APPLICATION

This application is a continuation-in-part of U.S. patent application Ser. No. 10/895,470 filed 19 Jul. 2004 now abandoned. This related application is incorporated by reference herein.

BACKGROUND

The following description relates to devices for detecting bacteria and more specifically to the use of phage or phages to detect bacteria.

Phages are viruses whose hosts are bacterial cells. The phage identify their hosts through specific receptor molecules located on the outside of the host cell. Once the phage find their specific receptors, they bind to the bacterial cell and inject their nucleic acid into the cell. This makes it possible to use phage to detect bacteria and, because phage binding can be so selective, it is possible to use phage to detect specific strains of a single bacterial species. For example, wildtype phage T4 can infect both *E. coli* strains B and K12 but a rII mutant of phage T4 will only infect *E. coli* strain B. Thus it is possible to ferret out a single bacterial strain among several strains.

Whiles antibodies have also been used to discriminate bacterial species, there are a number of advantages to using phage in place of antibodies. Antibodies are bare protein molecules. As such, they can potentially be a food source for bacteria, leading to false alarms (specificity errors) in antibody-based bacterial detection techniques.

Because many antibody-based field test kits are currently inadequate in ferreting out specific bacterial sources, the White House has advised caution in their use. This constraint has been imposed because false positives in the past have resulted in buildings being unnecessarily shut down and antibiotics being unnecessarily dispensed. Other limitations of such antibody-based immunoassays include antibody manufacturability and instability.

Phage on the other hand is widely available and in fact libraries of phage exist. One such library is the Felix D'Herelle Reference Center for Bacterial Viruses at Laval University in Quebec, Canada. This library has a collection of approximately 500 phages.

Phage is also very robust, and is not as sensitive to temperature, pH, and ionic strength as antibodies are. Once a phage for a given host has been identified, large quantities of phage can be easily manufactured and purified. The purified phage exhibits a long shelf life.

The use of phage as a bacteria sensor can take a number of forms. Phage can be coupled to magnetic microparticles that are in turn used to capture the host bacteria from an aqueous/air environment. Once captured, a magnet can be used to separate the captured bacteria from the rest of the sample matrix and to concentrate the captured bacteria onto an optical surface for detection.

Phage can also be coupled to optical fibers, glass, polymers, and quantum dots. In all such applications, a reliable method is needed to orient and bind the phage to these different substrates so that the phage can be effectively used as a bacteria sensor.

SUMMARY

A technique for orienting and binding the head end of phage to a substrate is disclosed. The tail end of the phage is thereby made available for bacteria sensing.

Other objects, advantages and new features will become apparent from the following detailed description when considered in conjunction with the accompanied drawings.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIGS. 3A and B show additional 1000× magnifications of DAPI stained and SYBR (TRADEMARK) Gold stained images, respectively.

DESCRIPTION

Figure 1A:
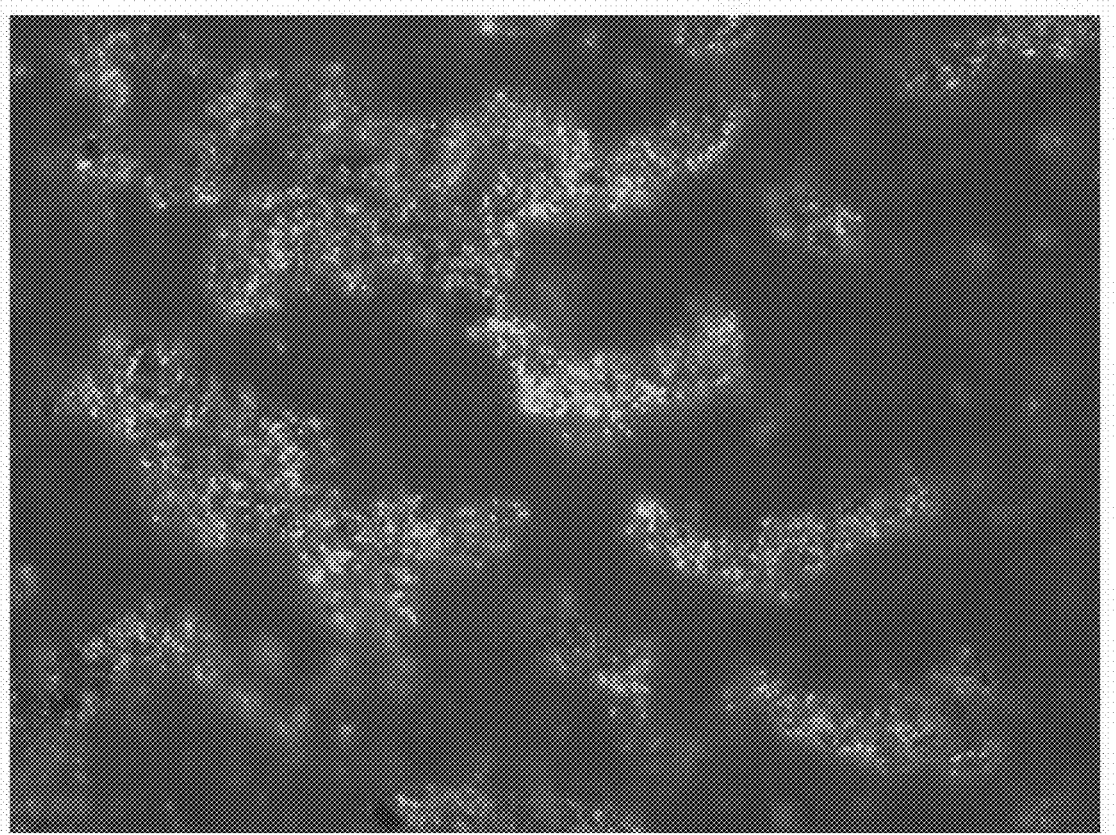
FIGS. 1A and B illustrate, respectively, epifluorescence microscope and transmission electron microscope images of phage bound to microparticles.

The following is an example. Phage (bacteriophage) lyzate is prepared, by inoculating two liters of nutrient broth containing a host bacteria with the phage. One commonly used nutrient broth is the Luria Bertani (LB) broth. Prior to inoculating with phage, the bacteria-broth suspension is cloudy. The phage-inoculated suspensions are incubated, with shaking at 37° C., until the suspensions become clear, indicating that the bacterial host cells have lyzed releasing phage progeny. Once clear, 5 mL of chloroform is added to lyze any remaining bacterial cells. The lyzate is then centrifuged to pelletize the bacterial DNA and cell constituents. The liquid above the pellet, which contains the bacteriophage, is then decanted. The molecular constituents of the broth include proteins, amino acids, carbohydrates, etc., which have the same functional groups as the phage used to bind to the magnetic silica-based microparticles. Consequently the molecular constituents of the broth can interfere with phage binding to the magnetic microparticles. The phage is therefore separated from the constituents of the nutrient broth and concentrated in phosphate buffer solution. This can be performed in a number of ways. One method utilizes a tangential filter, which employs size exclusion to separate the phage from the molecular constituents of the broth.

The construction of a phage-based biosorbent for *Salmonella* has been described in the past.[1] In this procedure, phage SJ2, whose host is *Salmonella*, was biotinylated and bound to streptavidin-labeled magnetic microspheres. The biotin derivative used for biotinylation, sulfosuccinimidobiotin, reacts with the phage surface protein through primary amines.

Use of the streptavidin-biotin coupling chemistry to immobilize phage onto magnetic microparticles has been explored in the inventor's laboratory. In these experiments, streptavidin-coated magnetic microparticles were mixed with a suspension of *Salmonella*. Streptavidin has no recognition elements specific for *Salmonella* or any other bacterial species. Yet, microscopic examination showed that the surface of the streptavidin-coated magnetic microparticle is covered with bacteria. Streptavidin is a known tetrameric protein. As such it can be a potential food source for bacteria. These results are indicative of bacterial 'grazing' of streptavidin, which will ultimately lead to an unacceptable number of false positives.

The above-cited paper describing this methodology of constructing a phage-based biosorbent indicates that nonspecific capture of bacteria on streptavidin-coated magnetic microparticles occurred.[1] Because of this nonspecificity, further pursuit of the streptavidin-biotin coupling chemistry was curtailed.

Other magnetic microparticles with different chemistries from that of the streptavidin-coated magnetic microparticles are also commercially available. One source for these is Bangs Laboratories (9025 Technology Dr., Fishers, Ind.). Such magnetic microparticles are in the shape of microspheres that are approximately 1 μm in diameter, contain 12-60% magnetite, and are available with the following reactive groups for coupling: carboxyl [—COOH], amine [—NH$_2$], hydroxy [—OH], hydrazide [—C(O)NHNH$_2$], epoxy [—(CH$_2$—$^O$CH$_2$)], sulfonate [—SO$_3$H], and benzyl chloride [—C$_6$H$_6$—CH$_2$Cl]. Of these, the most commonly used coupling reactions involve the use of carboxyl and amine functionalized magnetic microspheres. All of these functional groups bind to amine groups of the target.

Of these different micropsphere chemistries, the amine coupling chemistry was then explored by the inventors. In this methodology, amine-terminated magnetic microspheres are activated by reaction with glutaraldehyde. These activated magnetic microparticles then react with the primary amine groups of the ligand, in this case the phage T4 whose host is *E. coli*. The established coupling protocol for binding the phage onto amine terminated magnetic microparticles was then followed. After binding, a 10 μL sample of the magnetic microparticles was aliquoted into 5 mL of 1× Phosphate Buffered Saline (PBS) solution. An aliquot of 1 μL of stock SYBR (TRADEMARK) Gold DNA stain was added. This SYBR (TRADEMARK) Gold is available through Molecular Probes of Eugene, Oreg. After incubating for approximately 10 minutes at room temperature the sample was filtered onto a 0.2 μm pore size ANODISC (TRADEMARK) membrane. Upon mounting the membrane onto a microscope slide, it was analyzed using an epifluorescence microscope.

The results are summarized in FIG. 1A. The image shows bright, luminescent spheres on the magnetic microparticles. These bright, luminescent spheres are due to T4 phages that have been immobilized on the magnetic microparticles. The image shown in FIG. 1A indicates that the distribution of phage on the surface of the magnetic microparticles is fairly homogenous.

Figure 1B:
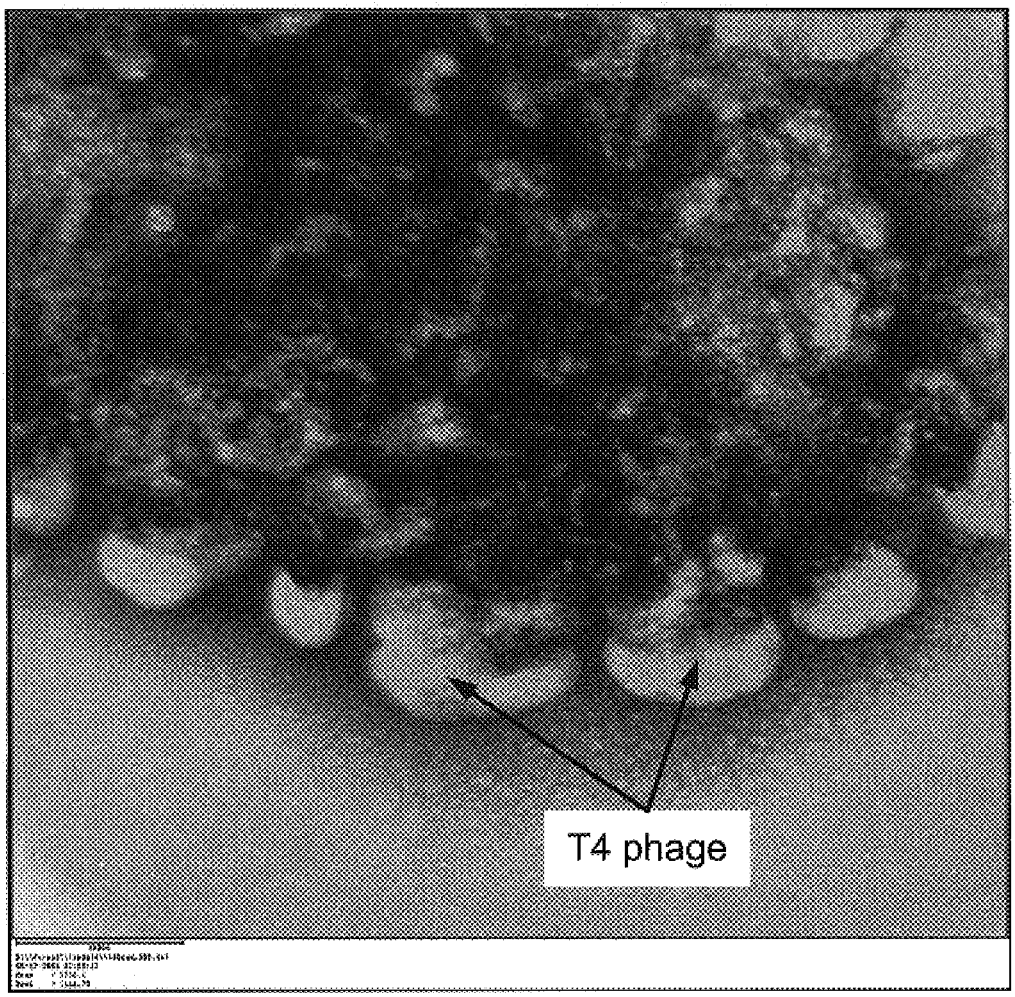

No capture, however, of *E. coli* was observed to occur when the phage bound magnetic microparticles were mixed with a suspension of the T4 host bacteria. To determine why capture was not occurring, the phage bound magnetic microparticles were subjected to Transmission Electron Microscope (TEM) analysis. The results are shown in FIG. 1B. The TEM image shows that, although the surface of the magnetic microparticle is covered with phage, the binding is preferentially through the tail end of the phage as opposed to the head end of the phage. Because the tail end is essentially blocked, the phage immobilized on the magnetic microparticles is non-receptive to the capture of their host bacteria.

Figure 2A:
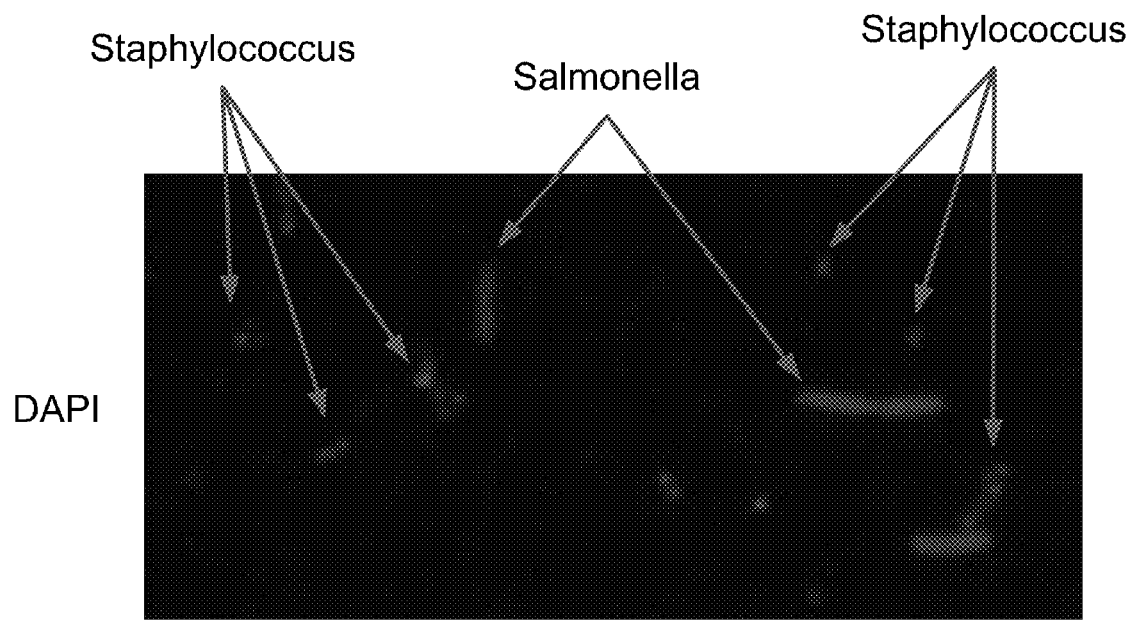
FIGS. 2A and B show 1000× magnifications of DAPI stained and SYBR (TRADEMARK) Gold stained images, respectively.
Figure 2B:

The inventors therefore embarked on determining how to immobilize phage on a substrate that preferentially binds the phage heads and not the phage tails to the substrate. As shown in FIGS. 2 (A and B) and FIGS. 3 (A and B), nucleic acid stains pass through the protein shell of the phage head and bind to the phage DNA/RNA.

Figure 4:
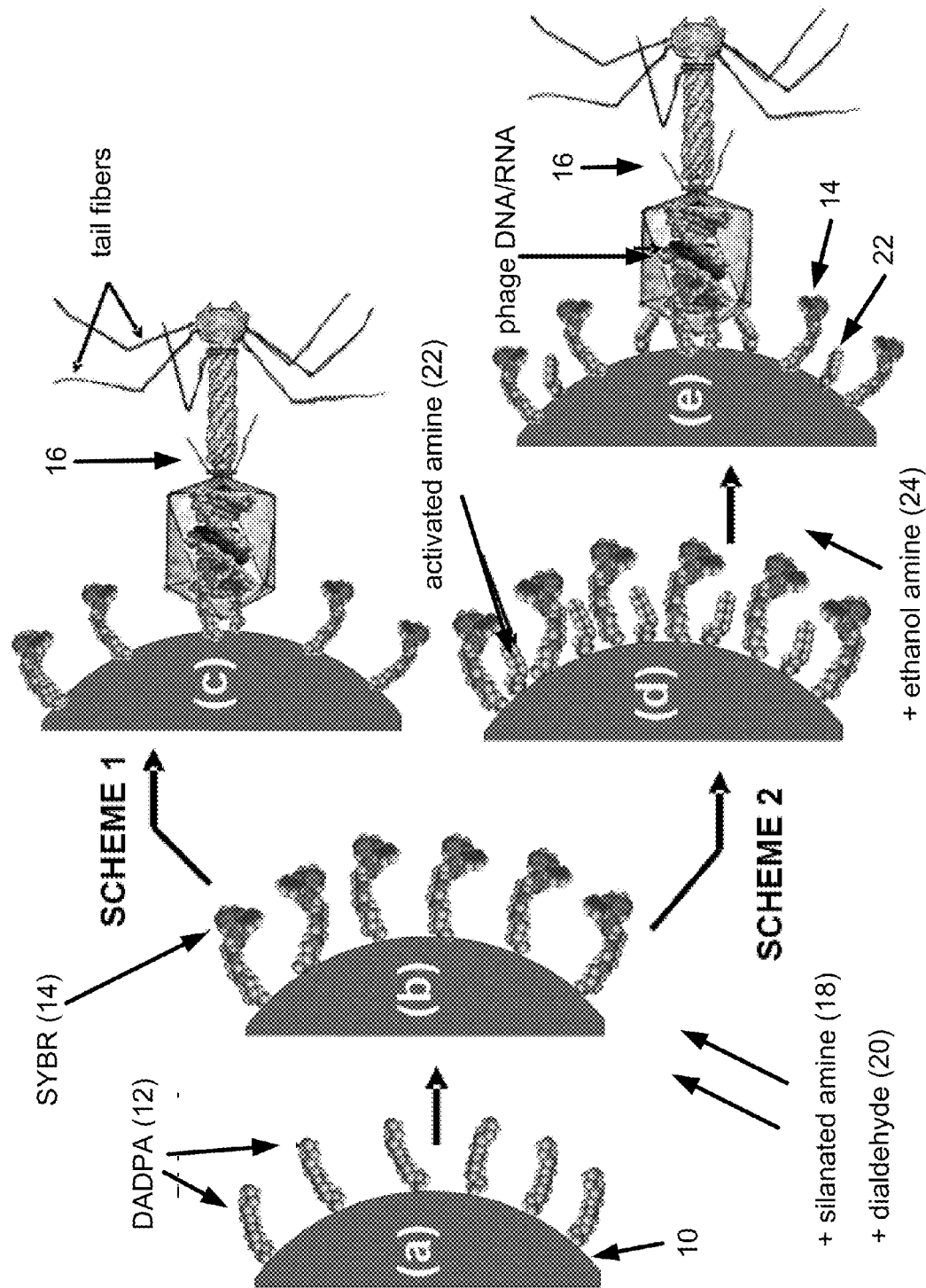
FIG. 4 illustrates two example schemes to orient and bind phage to microparticles.

FIG. 4 shows schematically two schemes to bind phage through its head to a silica-based substrate. Shown is a silica-based substrate 10, such as for example silica-based magnetic microspheres, having a long-chained alkyl amine immobilized 12 thereon, such as diaminodipropylamine (DADPA). An example of such a combination is commercially available through Bioclone, San Diego, Calif., in the form of diaminodipropylamine (DADPA)-modified magnetic microparticles. The DADPA functionality provides a long spacer length between the surface of the microparticle and the associated primary amine group.

A nucleic acid complexing agent 14, such as an unsymmetrical cyanine dye, is then bound to long-chained alkyl amine 12. An example of such an agent is an amine-reactive succinimidyl ester of SYBR (TRADEMARK), commercially available through Molecular Probes of Eugene, Oreg. Following standard protocols, the succinimidyl ester of SYBR (TRADEMARK) was bound to the primary amine group of DADPA 12.

Referring to SCHEME 1 of FIG. 4, a sample of purified phage 16, for example T4, was added to the SYBR (TRADEMARK)-derivatized DADPA magnetic microparticles and was allowed to react for approximately two hours. It should be noted that other phages, such as P22, may also be used. Afterwards, a 10 μL sample of the magnetic microparticles was aliquoted into 5 mL of 1×PBS solution. An aliquot of 10 μL of stock 4',6-Diamidino-2-phenylindole (DAPI) DNA stain was then added. After incubating for 10 minutes the sample was filtered onto a 0.2 μm pore size Anodisc membrane. The membrane was then mounted onto a microscope slide and was analyzed using an epifluorescence microscope. Luminescent spheres on the microparticles were observed that are attributed to T4 phages bound to the surface of the magnetic microparticle. When *E. coli* and the T4-immobilized magnetic microparticles were mixed together, no capture of the bacteria was observed. Additionally, microscopic examination showed the presence of free standing phage.

These results indicate that, although the DADPA functionality is long by chemical standards, it is fairly short by biological criterion. As a result, the phage were not rigidly held in place on the surface of the magnetic microparticles and could essentially 'pop' off the particle surface.

One way of improving the adhesion of the phage onto the microparticles is to lengthen the spacing between the surface of the microparticle and the primary amine group used to bind to the succinimidyl ester of SYBR (TRADEMARK). The SYBR (TRADEMARK) functionality will be able to penetrate deeper into the head of the phage and bind to the phage DNA/RNA. However, the chemistries that could be used to extend the DADPA chain lengths could also result in undesirable crosslinking within and between microparticles.

Another approach to improve adhesion between the phage and the surface of a silica-based microparticles is illustrated in SCHEME 2 of FIG. 4. This approach takes advantage of the fact that the DADPA terminated magnetic microparticles have a silica shell. After binding the SYBR (TRADEMARK) fluorophore to the DADPA moiety on the magnetic microparticles, a silanated amine 18, such as 3-aminopropyltrimethoxysilane (3-APTMS), is added to the vial. The silane portion of the 3-APTMS binds to the silica of the magnetic microparticles leaving a primary amine portion for binding to the phage. These primary amine groups are then activated by reaction with a dialdehyde 20 such as glutaraldehyde. With the addition of phage 16, the SYBR (TRADEMARK) moiety bound to the DADPA termination hold the phage in place by its head. With the phage head oriented towards the microparticle, activated amine groups 22 on the surface of the microparticles then bind to amine groups on the phage head. The remaining activated amine groups are then reacted with an alkyl-amine compound 24, such as ethanolamine, to provide a deactivated amine 22'. Microscopic examination of the microparticles shows the presence of luminescent spheres on the surface of the microparticles and are attributed to the bound phage.

In this procedure, the bound nucleic acid stain orients the phage head down on the surface of the substrate and the amine-coupling chemistry is used to create a strong, covalent, bond to the phage head—thereby immobilizing the phage on the surface. The activator used in the amine-coupling chemistry is not temperature or moisture sensitive. The concentrations of activator required is enough to assure that amine groups on the microspheres are saturated, thereby avoiding crosslinking between microspheres prior to binding to bacteriophage. In this process, the reagents used in the amine-coupling chemistry are not an attractive food source for bacteria and therefore will not cause false positives in the detection of bacteria.

BIBLIOGRAPHY

1. W. Sun, L. Brovko, and M. Griffiths, "*Use of Bioluminescent Salmonella for Assessing the Efficiency of Constructed Phage-Based Biosorbert*", J. Industrial Microbiology and Biotechnology, Vol. 27, p. 126 (2001).

Obviously, many modifications and variations are possible in light of the above description. It is therefore to be understood that within the scope of the claims, the invention may be practiced otherwise than as has been specifically described.

What is claimed is:

1. A phage binding and orientation method comprising the steps of:
   providing a long-chained alkyl amine immobilized on a silica-based substrate:
   binding a nucleic acid complexing agent to the long-chained alkyl amine, wherein the nucleic acid complexing agent is an unsymmetrical cyanine dye configured to penetrate a phage head and bind to nucleic acid therein;
   binding a silanated amine to the silica-based substrate, wherein a silane portion of the silanated amine binds to the silica-based substrate and a primary amine portion of the silanated amine is available upon activation for binding to phage having head and tail ends;
   activating the primary amine portion of the silanated amine by reaction with a dialdehyde;
   adding the phage, wherein the nucleic acid complexing agent binds to the nucleic acid within the phage head to orient the phage and the activated primary amine then binds to the phage head; and
   reacting any remaining activated primary amine portions of the silanated amine with an alkyl-amine compound.

2. The method according to claim 1 wherein said long-chained alkyl amine is diaminodipropylamine (DADPA).

3. The method according to claim 1 wherein said unsymmetrical cyanine dye has a succinimidyl ester group.

4. The method according to claim 1 wherein said silanated amine is 3-aminopropyltrimethoxysilane (3-APTMS).

5. The method according to claim 1 wherein said dialdehyde is glutaraldehyde.

6. The method according to claim 1 wherein said alkyl-amine compound is ethanolamine.

7. The method according to claim 1 wherein said phage is T4.

8. The method according to claim 1 wherein said silica-based substrate is a microparticle.

9. The method according to claim 8 wherein said microparticle is a magnetic microparticle.

10. A phage binding and orientation method comprising the steps of:
    providing diaminodipropylamine (DADPA) immobilized on a silica-based substrate;
    binding an unsymmetrical cyanine dye fluorophore to the DADPA;
    binding 3-aminopropyltrimethoxysilane (3-APTMS) to the silica-based substrate, wherein a silane portion of the 3-APTMS binds to the silica-based substrate and a primary amine portion of the 3-APTMS is available upon activation for binding to phage;
    activating the primary amine portion of the 3-APTMS by reaction with glutaraldehyde;
    adding the phage, wherein the phage has head and tail ends and the head end of the phage is held by the unsymmetrical cyanine dye fluorophore bound to the DADPA to orient the phage and the activated amine then binds to amine on the phage head; and
    reacting any remaining activated amine portions of the 3-APTMS with ethanolamine.

11. The method according to claim 10 wherein said silica-based substrate is a DADPA terminated microparticle.

12. The method according to claim 11 wherein said DADPA terminated microparticle is a magnetic microparticle.

13. The method according to claim 10 wherein said unsymmetrical cyanine dye fluorophore includes a succinimidyl ester.

14. The method according to claim 10 wherein said phage is T4.

15. A phage binding and orientation method comprising the steps of:
    providing diaminodipropylamine (DADPA) immobilized on a silica-based microparticle;
    binding an unsymmetrical cyanine dye fluorophore to the DADPA;
    binding 3-aminopropyltrimethoxysilane (3-APTMS) to the silica-based microparticle, wherein a silane portion of the 3-APTMS binds to the silica and a primary amine portion of the 3-APTMS is available upon activation for binding to phage;
    activating the primary amine portion of the 3-APTMS by reaction with glutaraldehyde;
    adding the phage, wherein the phage has head and tail ends and the head end of the phage is held by the unsymmetrical cyanine dye fluorophore bound to the DADPA to orient the phage and the activated amine binds to amine on the phage head; and
    reacting any remaining activated amine portions of the 3-APTMS with ethanolamine.

16. The method according to claim 15 wherein said DADPA microparticle is a magnetic microparticle.

17. The method according to claim 15 wherein said phage is T4.

18. The method according to claim 1 wherein said phage is P22.

19. The method according to claim 10 wherein said phage is P22.

20. The method according to claim 15 wherein said phage is P22.

* * * * *